(12) United States Patent
Vallittu et al.

(10) Patent No.: US 6,733,288 B2
(45) Date of Patent: May 11, 2004

(54) ORTHODONTIC APPLIANCE

(75) Inventors: Pekka Vallittu, Kuusisto (FI); Lippo Lassila, Turku (FI); Ilkka Kangasniemi, Turku (FI)

(73) Assignee: Stick Tech Oy, Turku (FI)

( * ) Notice: Subject to any disclaimer, the term of this patent is extended or adjusted under 35 U.S.C. 154(b) by 0 days.

(21) Appl. No.: 10/133,656

(22) Filed: Apr. 29, 2002

(65) Prior Publication Data

US 2003/0203333 A1 Oct. 30, 2003

(51) Int. Cl.[7] .................................................. A61C 3/00
(52) U.S. Cl. ........................................... 433/20; 433/24
(58) Field of Search ............................. 433/8, 9, 10, 20, 433/24

(56) References Cited

U.S. PATENT DOCUMENTS

| | | | | |
|---|---|---|---|---|
| 3,178,822 A | * | 4/1965 | Fogel et al. ................ | 433/20 |
| 4,180,911 A | * | 1/1980 | Bullock ...................... | 433/9 |
| 4,516,938 A | * | 5/1985 | Hall ........................... | 433/9 |
| 4,533,320 A | * | 8/1985 | Piekarsky .................. | 433/9 |
| 4,717,341 A | | 1/1988 | Goldberg et al. .......... | 433/9 |
| 4,894,012 A | | 1/1990 | Goldberg et al. .......... | 433/215 |
| 4,932,866 A | * | 6/1990 | Guis ............................ | 433/24 |
| 5,318,440 A | | 6/1994 | Adam et al. ................ | 433/8 |
| 5,564,929 A | | 10/1996 | Alpert ........................ | 433/224 |
| 5,759,029 A | | 6/1998 | Kobayashi et al. ........ | 433/20 |
| 5,797,748 A | | 8/1998 | Reynaud et al. ........... | 433/224 |
| 5,987,376 A | | 11/1999 | Olson et al. ................ | 701/201 |
| 2001/0001510 A1 | | 5/2001 | Rheinberger et al. ..... | 264/17 |
| 2001/0036617 A1 | | 11/2001 | Karmnaker et al. ....... | 433/173 |

* cited by examiner

Primary Examiner—Cary E. O'Connor
(74) Attorney, Agent, or Firm—James C. Lydon

(57) ABSTRACT

The use of a prepreg containing at least one fiber and a matrix to be cured during application, for the production of a fiber-reinforced composite, for active orthodontic therapy. An active orthodontic appliance is disclosed which includes an arch wire in at least one part, directly contactable with teeth and including a fiber-reinforced composite containing at least one fiber and a matrix, the arch wire including a loop directly contactable with a tooth or teeth to be moved by the appliance. A process for manufacturing an active orthodontic appliance and to an active orthodontic method of treatment are also disclosed.

24 Claims, 6 Drawing Sheets

ORTHODONTIC APPLIANCE

FIELD OF THE INVENTION

The present invention relates to the use of a prepreg for the production of a composite and to an active orthodontic method of treatment. The invention further relates to an active orthodontic appliance comprising an arch wire consisting essentially of a fiber-reinforced composite comprising at least one fiber and a matrix, as well as to a process for manufacturing an active orthodontic appliance.

BACKGROUND OF THE INVENTION

In active orthodontic treatment teeth are rearranged by removable or fixed orthodontic appliances in order to achieve better occlusal stability, function as well as appearance. Orthodontic treatment is based on the principle that if prolonged pressure is applied to a tooth, tooth movement will occur as the bone around the tooth remodels. Tooth movement can be bodily movement, tipping, root uprighting, rotation, extrusion or intrusion.

The state-of-the-art methods to move teeth are based on using fixed orthodontic appliances. These appliances comprise metallic or ceramic brackets adhered to the teeth and a metal arch wire (e.g. nickel-titanium alloy), which is bent in such a way that it transfers a desired force to the teeth. Shortcomings of the state-of-the-art method are e.g. structural complicity of the appliances which can cause oral hygiene problems resulting in decay, and poor appearance of the appliance. To overcome the appearance problem, tooth colored ceramic brackets and fiber-reinforced composite brackets (Adam et al, U.S. Pat. No. 5,318,440) have been introduced. However, despite the development of the bracket materials, one problem still occurs, i.e. the quite frequent loosening of the brackets from the tooth surface. The problem is due to the fact that high strength metals and ceramics (such as titanium alloys and zirconium oxides) are difficult to adhere to the tooth surface in clinical conditions.

Recently, fiber-reinforced composites (FRC) have been introduced for dental use. One application of FRCs is to replace metal wires used as an orthodontic arch wires. This has been described by Kusy & Kennedy (U.S. Pat. No. 5,987,376), Goldberg & Burstone (U.S. Pat. No. 4,717,341) and Kobayashi et al (U.S. Pat. No. 5,759,029). The system uses continuous unidirectional glass fiber wire as a translucent, i.e. aesthetic, arch wire in combination with traditional brackets. In all of these inventions, a cured FRC arch wire, i.e. FRC arch wire with a finally polymerized matrix, and brackets is used.

OBJECT OF THE INVENTION

The object of the invention is to provide an active orthodontic appliance that does not have the above-mentioned drawbacks. It is thus an object of the invention to provide an appliance having a simple, reliable and aesthetic structure, which allows the maintenance of good oral hygiene.

Another object of the invention is to provide an active orthodontic appliance that may be attached to teeth without using brackets. An object of the invention is also to provide a process for manufacturing said appliance. Yet another object of the invention is to provide a novel use for a prepreg as well as to provide a new method of active orthodontic treatment.

SUMMARY OF THE INVENTION

The invention relates to the aspects defined in the annexed claims.

The invention relates to the use of a prepreg comprising at least one fiber and a matrix to be cured during application, for the production of a fiber-reinforced composite, for active orthodontic therapy.

The invention further relates to an active orthodontic appliance consisting essentially of an arch wire in at least one part, directly contactable with teeth and consisting essentially of a fiber-reinforced composite comprising at least one fiber and a matrix, said arch wire comprising a loop directly contactable with a tooth or teeth to be moved by the appliance.

The invention also relates to a process for manufacturing an active orthodontic appliance comprising the steps of:

a) shaping a first portion of a prepreg consisting of a composition comprising at least one fiber and a matrix in its non-cured form, to the shape of the tooth or teeth to be used as support for the appliance, b) shaping a second portion of the prepreg to the shape of the tooth or teeth to be obtained by the appliance, c) curing said prepreg to obtain a composite, and d) forcing the second portion of the composite obtained to the original shape of the tooth or teeth to be moved by the appliance.

The invention still relates to an active orthodontic method of treatment comprising the steps of a) shaping a first portion of a prepreg consisting of a composition comprising at least one fiber and a matrix in its non-cured form, to the shape of the tooth or teeth to be used as support, b) shaping a second portion of the prepreg to the shape at the end of the orthodontic treatment, c) curing said prepreg to obtain a composite, d) forcing said second portion of the composite to the shape at the beginning of the orthodontic treatment to obtain an orthodontic appliance, and e) contacting said appliance to said teeth for the duration of said treatment.

DETAILED DESCRIPTION OF THE INVENTION

In this application, by curing it is meant polymerization and/or crosslinking. By matrix, it is understood the continuous phase of the composition and by matrix in its non-cured form it is meant a matrix that is in its deformable state but that can be cured, i.e. hardened, to a non-deformable state. The matrix in its non-cured form may already comprise some long chains but it is essentially not yet polymerized. By prepreg, it is meant a semi-manufactured product, that is, a product that is non or partly polymerized yet still deformable. The polymerization of a prepreg leads to a composite. The words "composite" and "cured prepreg" may be used interchangeably.

The invention relates to the use of a prepreg comprising at least one fiber and a matrix to be cured during application, for the production of a fiber-reinforced composite, for active orthodontic therapy.

By application, it is meant the manufacturing of an active orthodontic appliance, that is, the operation performed by a dentist or a dental technician to provide an appliance suitable for specific needs of the patient, starting from a prepreg. The manufacturing comprises also the assembly of the device from semi-finished products and the curing to obtain said device.

The main difference of the present invention with the prior art is that in the present invention, the prepreg is cured to composite during the manufacturing of the appliance itself, whereas in the prior art, the prepreg is first cured to form a composite and thereafter the appliance is manufactured from said composite.

According to an embodiment of the invention, said composite is for direct contact to the teeth involved in said active orthodontic therapy. The composite of the invention may therefore be used in an orthodontic appliance without brackets, thus achieving one of the objects of the invention. The appliance may be attached to the teeth by means of dental adhesive, for example.

The invention further relates to an active orthodontic appliance consisting essentially of an arch wire in at least one part, directly contactable with teeth and consisting essentially of a fiber-reinforced composite comprising at least one fiber and a matrix, said arch wire comprising a loop directly contactable with a tooth or teeth to be moved by the appliance.

The appliance according to the invention thus has a simple and reliable structure allowing the maintenance of good oral hygiene. In addition, the appliance according to the invention is aesthetic since it does not require brackets and it is possible to make the appliance of the same color as the patient's teeth, so that the appliance is almost invisible. A further advantage of the appliance according to the invention is the increased convenience and comfort to the patient, due to the lack of brackets.

In summary, it can be said that the activation of the present inventive arch wire to move the teeth is obtained by polymerizing the fully impregnated prepreg's matrix to the desired form before adhering the inventive arch wire to the tooth enamel surface. After polymerization by e.g. light or laser, the arch wire is bent and attached to the tooth surface by means of dental adhesives, for example. It is also possible to attach the appliance to the teeth only once the whole appliance is ready. The bending causes internal stresses to the inventive arch wire, which are going to move the tooth to the desired location, as the arch wire tends to return to its original shape.

According to an embodiment of the invention, the arch wire is in one part and according to another embodiment the arch wire is in at least two parts. When the arch wire is in one part, it forms a loop that is either attached to the tooth or teeth to be moved or passed over it, in which case it does not necessarily need to be attached, the contact together with the stress is enough to keep it in place during the treatment. The arch wire may also be in two or more parts. In this case, the first part of the arch wire is formed to the position desired at the end of the treatment. The tooth or teeth to be moved is/are then connected to the first part of the arch wire by a second (and optionally further) part(s) of the arch wire. More complicated misalignment of teeth may be corrected with this kind of appliance than when the arch wire is in one part. The first and further parts of the arch wire are thus in an angle with respect to each other. This embodiment will be further illustrated in the Figures below.

According to an embodiment of the invention, the orthodontic appliance is attached to each individual tooth by means of a dental adhesive.

The fiber or fibers used in the composition may be any fiber known per se and a person skilled in the art will be able to readily assess which fiber is the most suitable for the intended application. The choice of the fibers depends on the force needed for the movement of the teeth and the esthetic demands. Some examples of suitable fibers are glass fibers (S and E), silica fibers, quartz fibers, carbon fibers, ceramic fibers, polyolefin fibers, fibers prepared from copolymers of olefins, aramide fibers, polyester fibers, polyamide fibers, polyacrylic fibers. One composition may comprise one or more different types of fibers. The proportion of the fibers in the resin matrix should be preferably chosen so to give desired flexural properties to the appliance, i.e. tooth moving force after being activated after light polymerization in situ or chair-side and bending. The suitable volume fractions of the fibers vary between 10 and 70%.

The composition may comprise one, two, three, four, five, six or more continuous or semi-continuous fibers and/or staple, i.e. short, fibers. Preferably, the length of the fibers is at least 5 mm. By semi-continuous fibers it is meant that the fibers are shorter than the largest dimension of the resulting appliance and that at least two separate groups of fibers exist in the direction of said largest dimension. These at least two groups may overlap. The suitable diameter of the fiber(s) will also be evident to a person skilled in the art. Furthermore, the fibers may be used individually or in bundles. The fibers may also be in several bundles. The most appropriate configuration of the fibers will be obvious to a person skilled in the art in view of the result to achieve. Some examples of the configurations are given below in connection with the drawings.

According to a preferred embodiment of the invention, the fibers or fiber bundles are at a first distance from each other on the tooth enamel surface and at a second distance from each other between the teeth and that said second distance is essentially smaller than said first distance. In other words, the fibers or fiber bundles are spread on the tooth surface and in tight groups between the teeth, i.e. between the points of attachment to the teeth. The tight group form after having been polymerized to the desired location is the active part of the appliance forcing the tooth to be moved.

According to yet another embodiment of the invention, the orientation of the fibers of said prepreg are continuous unidirectional, bi-directional, tri-directional or any combination thereof. Generally, continuous unidirectional fibers are preferred due the high strength and high modulus properties in one direction (anisotropic materials). However, in applications where for example torque forces are needed, a combination of unidirectional fibers and bi-directional fibers result in more suitable tooth torque forces. This may be achieved by the configuration mentioned above in relation with the arch wire in two or more parts. In general, a person skilled in the art will be able to define the proper assembly of fiber groups in order to obtain the desired force in proper direction and amount.

The matrix used in the composition may be made of known monomer, dendrimer, oligomer or polymer and a person skilled in the art will be able to readily assess which material is the most suitable for the intended application. Some examples of suitable the matrix in its non-cured form are mono-, di-, tri- or multifunctional acrylates or methacrylates such as methyl methacrylate, ethyleneglycol dimethacrylate, bis-hydroxy-methacryloxyphenyl propane, triethyleneglycol dimethacrylate, polymethyl methacrylate, urethan dimethacrylate, as well as epoxies, esters, acrylics, sulfones, carbonates, dendrimers and combinations thereof. Dendrimers having 5 to 35 functional groups such as methacrylate or acrylate groups are preferred. Multifunctionality forms highly cross-linked matrix and decreases the creep of the polymer in the long-term use of the present appliance.

Examples of suitable dendrimers are given for example in U.S. Pat. No. 5,834,118 that is incorporated herein by reference. Dendrimers may particularly be startburst or hyperbranched methacrylated polyesters.

The curing in the invention is performed by a known curing process suitable for the selected matrix. The curing may be induced for example by electromagnetic radiation independently selected from the group consisting of visible light, ultra-violet light, blue light and laser irradiation. The wording "independently selected" means that different radiations may be used in different steps of the method. According to another embodiment, said matrix is autopolymerizable and the curing is induced by applying an activator on the prepreg. It is also possible to use matrixes that are stored in low temperatures (under room temperature or below 0° C.) after manufacturing and that autopolymerize once the temperature is increased to room temperature. The preferable polymerization initiation is obtained by radiation with blue light or by laser by help of initiators and activators for the free radical polymerization.

It is obvious to a person skilled in the art that the combination of fiber(s) and matrix need to be chosen so that the mechanical properties of the resulting appliance are suitable for intended use. By mechanical properties it is meant here for example the flexural properties, creep properties and tensile strength properties.

The invention also relates to a process for manufacturing an active orthodontic appliance comprising the steps of:

a) shaping a first portion of a prepreg consisting of a composition comprising at least one fiber and a matrix in its non-cured form, to the shape of the tooth or teeth to be used as support for the appliance, b) shaping a second portion of the prepreg to the shape of the tooth or teeth to be obtained by the appliance, c) curing said prepreg to obtain a composite, and d) forcing the second portion of the composite obtained to the original shape of the tooth or teeth to be moved by the appliance.

According to the an embodiment of the invention, the process further comprises a second curing step e) after the step a) and before the step b) in which step said first portion of the prepreg is cured to obtain a first portion of a composite. The prepreg may thus be cured in one or two parts. It is obvious to a person skilled in the art that the prepreg may also be cured in more that two distinct steps of process.

The appliance may be manufactured either outside the mouth, i.e. shaped on a model and then attached to the teeth, or in situ, i.e. in the mouth of the patient.

The fibers and matrix used in the composition as well as the curing processes have been discussed above in connection with the appliance and the use of the prepreg.

The invention still relates to an active orthodontic method of treatment comprising the steps of:

a) shaping a first portion of a prepreg consisting of a composition comprising at least one fiber and a matrix in its non-cured form, to the shape of the tooth or teeth to be used as support, b) shaping a second portion of the prepreg to the shape at the end of the orthodontic treatment, c) curing said prepreg to obtain a composite, d) forcing said second portion of the composite to the shape at the beginning of the orthodontic treatment to obtain an orthodontic appliance, and e) contacting said appliance to said teeth for the duration of said treatment.

According to an embodiment of the inventive method of treatment, it further comprises a step f) between steps a) and b) consisting of curing said first portion of the prepreg to obtain a first portion of a composite.

According to another embodiment of the invention, said method further comprises a step g) between steps b) and c) consisting of attaching said first portion of the composite to the tooth or teeth.

According to another embodiment of the invention, said composite is directly in contact with said tooth or teeth. The composite may thus be either directly attached to said tooth or teeth or it may form a loop that is passed over the tooth or teeth, thereby not requiring the attachment of the composite.

According to yet further embodiments of the invention, the composite is in steps f) and/or g) attached to each individual tooth by means of a dental adhesive.

The fibers and matrix used in the composition as well as the curing processes have been discussed above in connection with the appliance and the use of the prepreg.

DETAILED DESCRIPTION OF THE DRAWINGS

The Figures are schematic. The lines in the Figures that have below been referred to as fibers may as well be fiber bundles and in any case, said fibers or fiber bundles also comprise the matrix which is either to be cured or is already cured.

Figure 1:
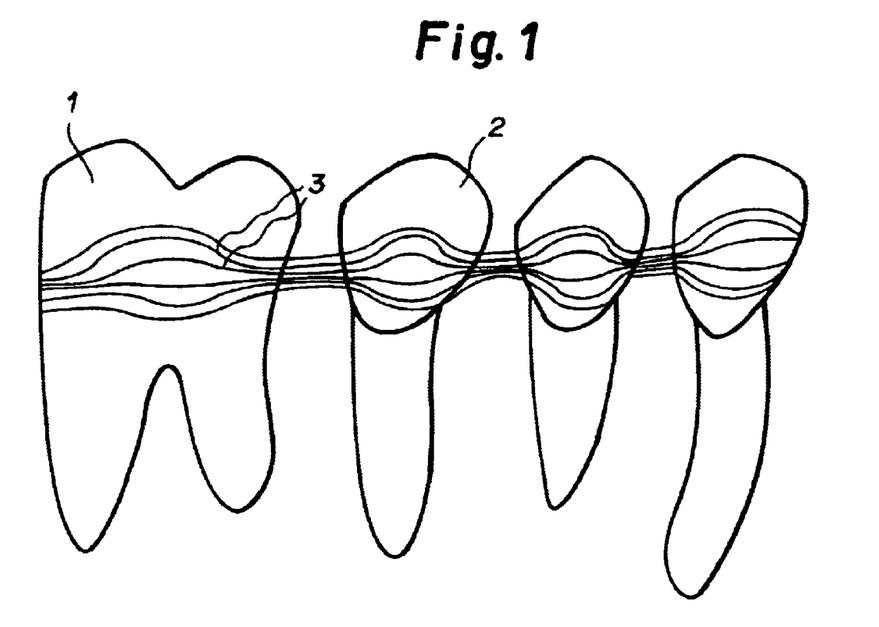
FIG. 1 illustrates an active orthodontic appliance according to a first embodiment of the invention.

FIG. 1 illustrates an active orthodontic appliance according to a first embodiment of the invention. The orthodontic appliance in this Figure is schematically presented in its final position and shape at the end of the active orthodontic treatment. The Figure shows teeth 1 and 2 as well as fibers 3. The fibers 3 are at a distance from each other, i.e. spread, on the parts of the appliance that are attached to the teeth and in bundles between the teeth. This configuration allows a good adherence of the appliance to the teeth. As can be seen from the Figure, the appliance according to the invention does not require the use of brackets.

Figure 2:
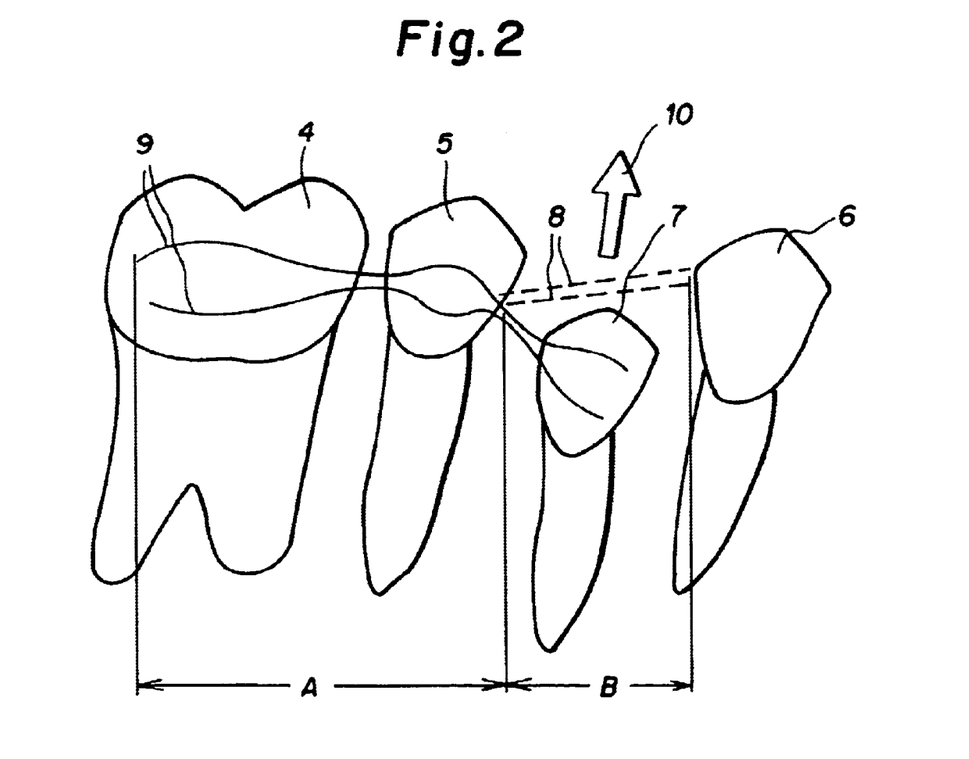
FIG. 2 illustrates an active orthodontic appliance according to a second embodiment of the invention.

FIG. 2 illustrates an active orthodontic appliance according to a second embodiment of the invention. The Figure shows teeth 4, 5, 6 and 7, the teeth 4 and 5 being the support teeth and the tooth 7 being the one to be moved during the active orthodontic treatment in the direction of the arrow 10. The appliance is manufactured either outside the mouth i.e.

shaped on a model and then attached to the teeth, or in situ, i.e. in the mouth of the patient.

In a first step, a prepreg is prepared from a composition comprising at least one fiber and a matrix in its non-cured form. Suitable prepregs are also available in the market. In a second step, a first portion of the prepreg is formed to the shape of the support teeth 4 and 5 and cured. The first portion is shown in FIG. 2 approximately by the area A. In a third step, a second portion of the prepreg is formed to the shape desired at the end of the orthodontic treatment and cured. The second portion is shown in. FIG. 2 approximately by the area B. The dashed lines 8 show the shape of the fibers 9 and the matrix as cured.

In a fourth step, said second portion of the cured prepreg, i.e. composite is forced to the shape at the beginning of the orthodontic treatment to obtain an orthodontic appliance, and it is attached to the teeth for the duration of the treatment. The attachment is preferably made with dental adhesive. The shape at the beginning of the orthodontic treatment is shown by the full lines on the tooth 7. The internal stresses in the composite caused by the bending forces the tooth to extrude to direction 10.

Figure 3:
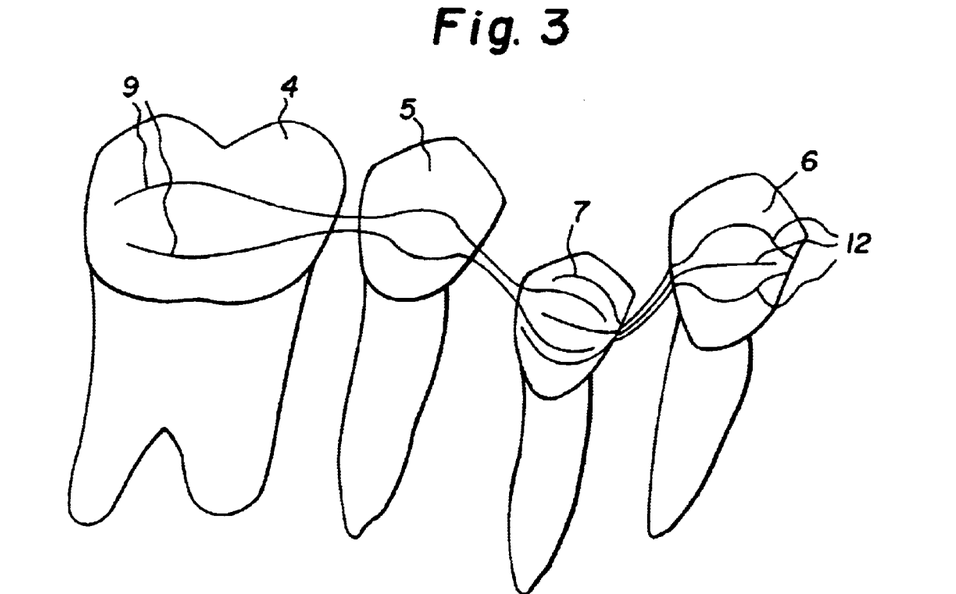
FIG. 3 illustrates an active orthodontic appliance according to a third embodiment of the invention.

FIG. 3 illustrates an active orthodontic appliance according to a third embodiment of the invention. The Figure shows teeth 4, 5, 6 and 7, the teeth 4, 5 and 6 being the support teeth and the tooth 7 being the one to be moved during the active orthodontic treatment. In this fourth embodiment, the finished orthodontic appliance is formed of two sets of fibers with matrix which are not cross-linked to each other. The first set 9 is identical to that of the second embodiment and it is prepared as disclosed above in connection with FIG. 2. The active force is directed as in FIG. 2 and the two sets of fibers which are not cross-linked to each other slide beside each other during the tooth movement. The second set of fibers with matrix 12 is prepared in the same manner as the first set. The two sets of fibers in this Figure are different from the two parts of the arch wire as discussed above.

Figure 4:
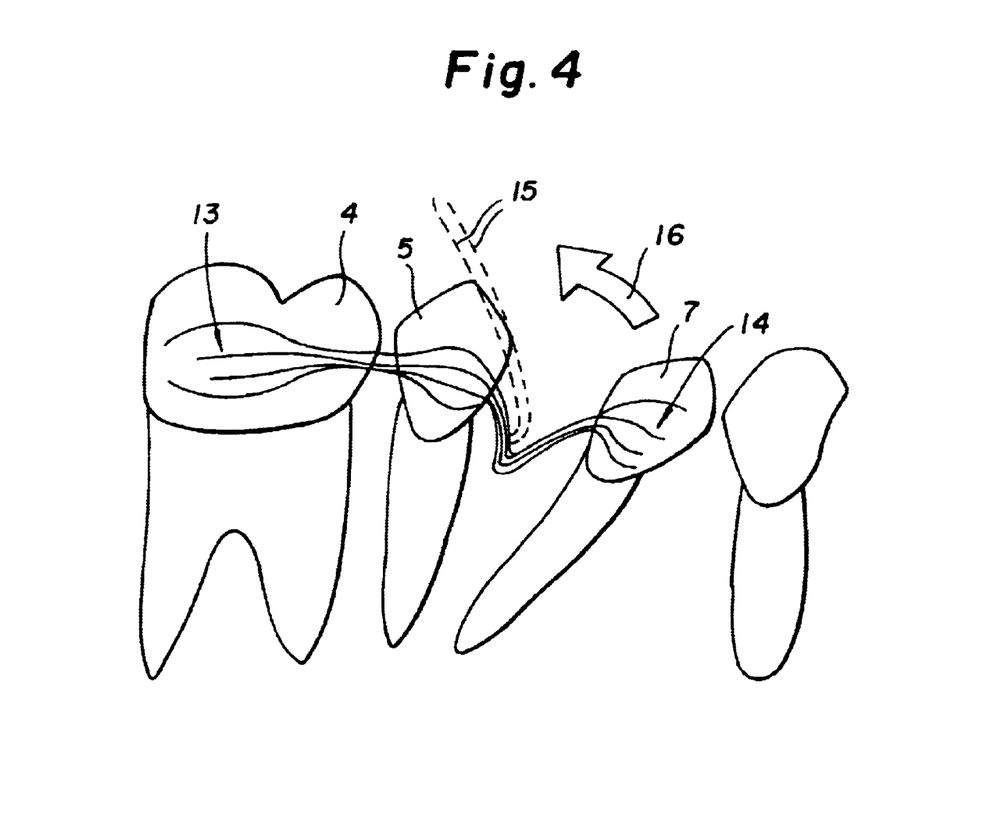
FIG. 4 illustrates an active orthodontic appliance according to a fourth embodiment of the invention.

FIG. 4 illustrates an active orthodontic appliance according to a fourth embodiment of the invention. This shows another kind of tooth misalignment to be solved by the appliance according to the invention. Indeed, when the first portion of the prepreg 13 has been cured and attached to the supporting teeth 4 and 5, the second portion of the prepreg 14 is formed and cured to the shape shown in dashed lines 15. Said second portion is then forced to the shape at the beginning of the treatment by attaching it to the tooth 7 to be moved during the treatment in the direction of the arrow 16.

Figure 5:
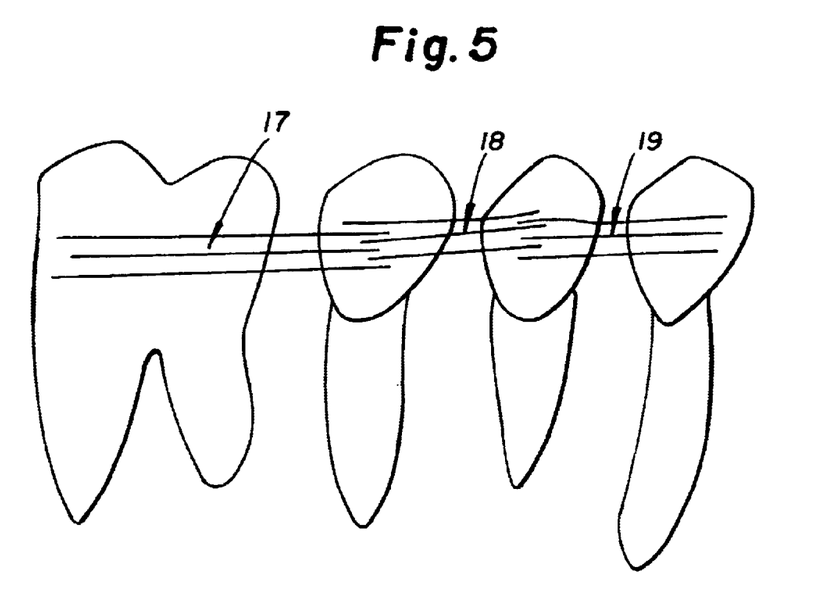
FIG. 5 illustrates an active orthodontic appliance according to a fifth embodiment of the invention.

FIG. 5 illustrates an active orthodontic appliance according to a fifth embodiment of the invention. In this embodiment, the appliance consists of three sets of fibers 17, 18 and 19, which overlap each other. In this embodiment, the fibers are neither bundled between the teeth, nor cross-linked to each other. Creeping of the non cross-linked matrix allows the fiber sets to slide beside each other. Within the set of fibers, the matrix is cross-linked.

Figure 6:
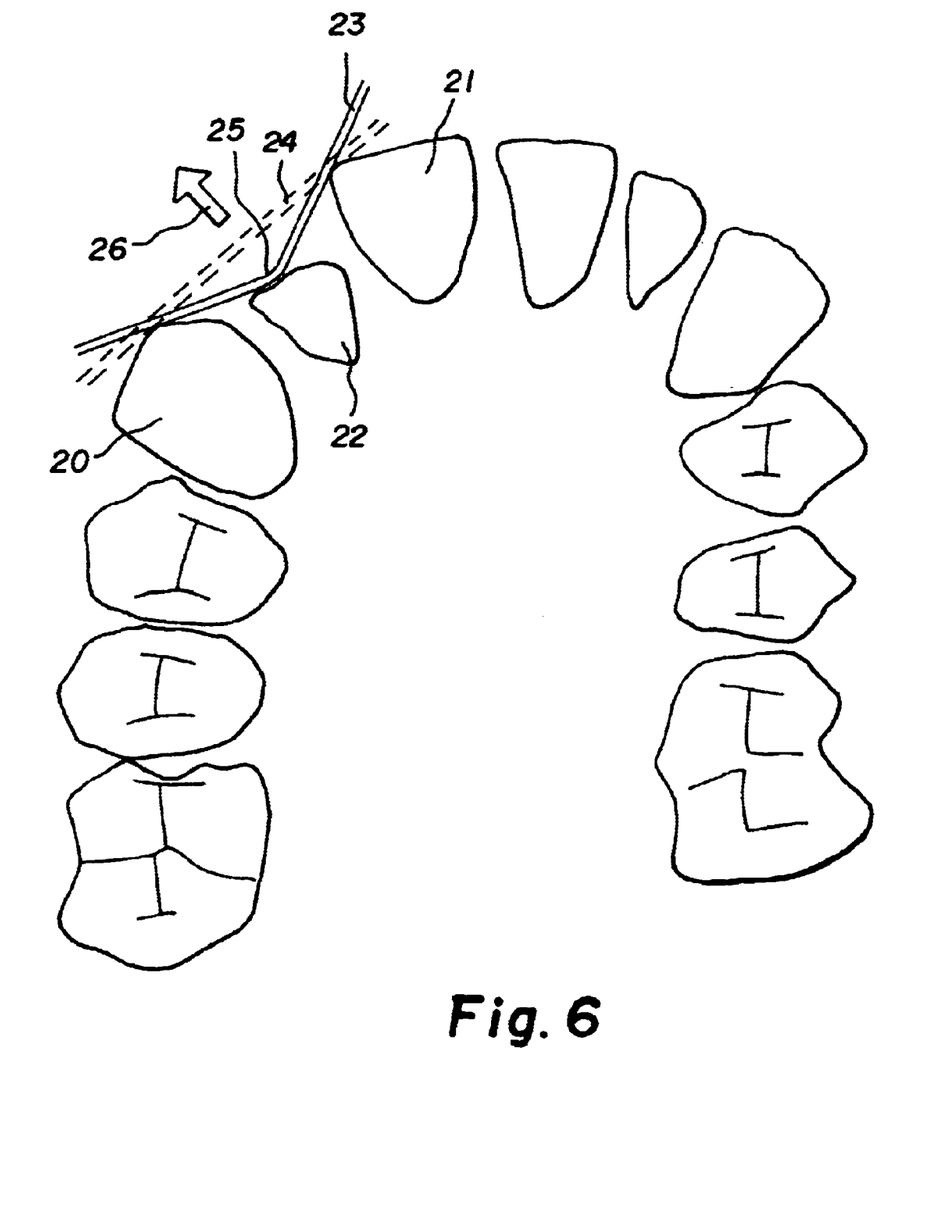
FIG. 6 illustrates an active orthodontic appliance according to a sixth embodiment of the invention.

FIG. 6 illustrates an active orthodontic appliance according to a sixth embodiment of the invention in an occlusal view. The Figure shows the support teeth 20 and 21 and the tooth 22 to be moved during the active orthodontic treatment. In this embodiment, the arch wire 23 is in one part and after being polymnerized to straight form (showed in dash line 24), it is forced to the form shown and adhered to the tooth 22 at the point 25. This forcing (bending) causes stress to the appliance which moves the tooth in the direction shown by the arrow 26.

Figure 7:
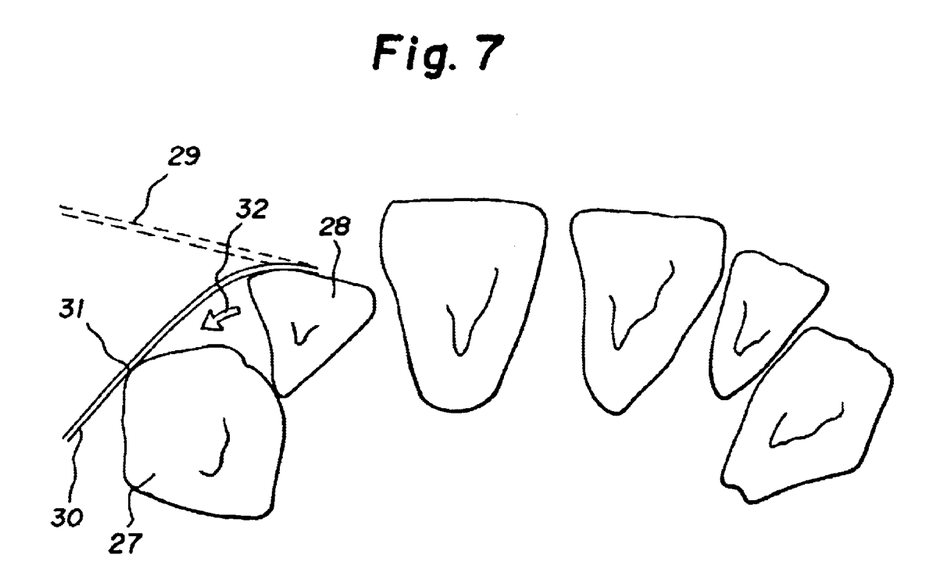
FIG. 7 illustrates an active orthodontic appliance according to a seventh embodiment of the invention.

FIG. 7 illustrates an active orthodontic appliance according to a seventh embodiment of the invention. The Figure shows the situation where the tooth 27 is used as an anchor to rotate the tooth 28. The prepreg is firstly adhered to the tooth 28 and polymerized to the form shown by the dashed lines 29. After polymerization, the appliance is bended so as it to have the form shown in 30 and adhered to the tooth 27 at point 31. As a result, a force in the direction of the arrow 32 is applied to the tooth 28.

Figure 8:
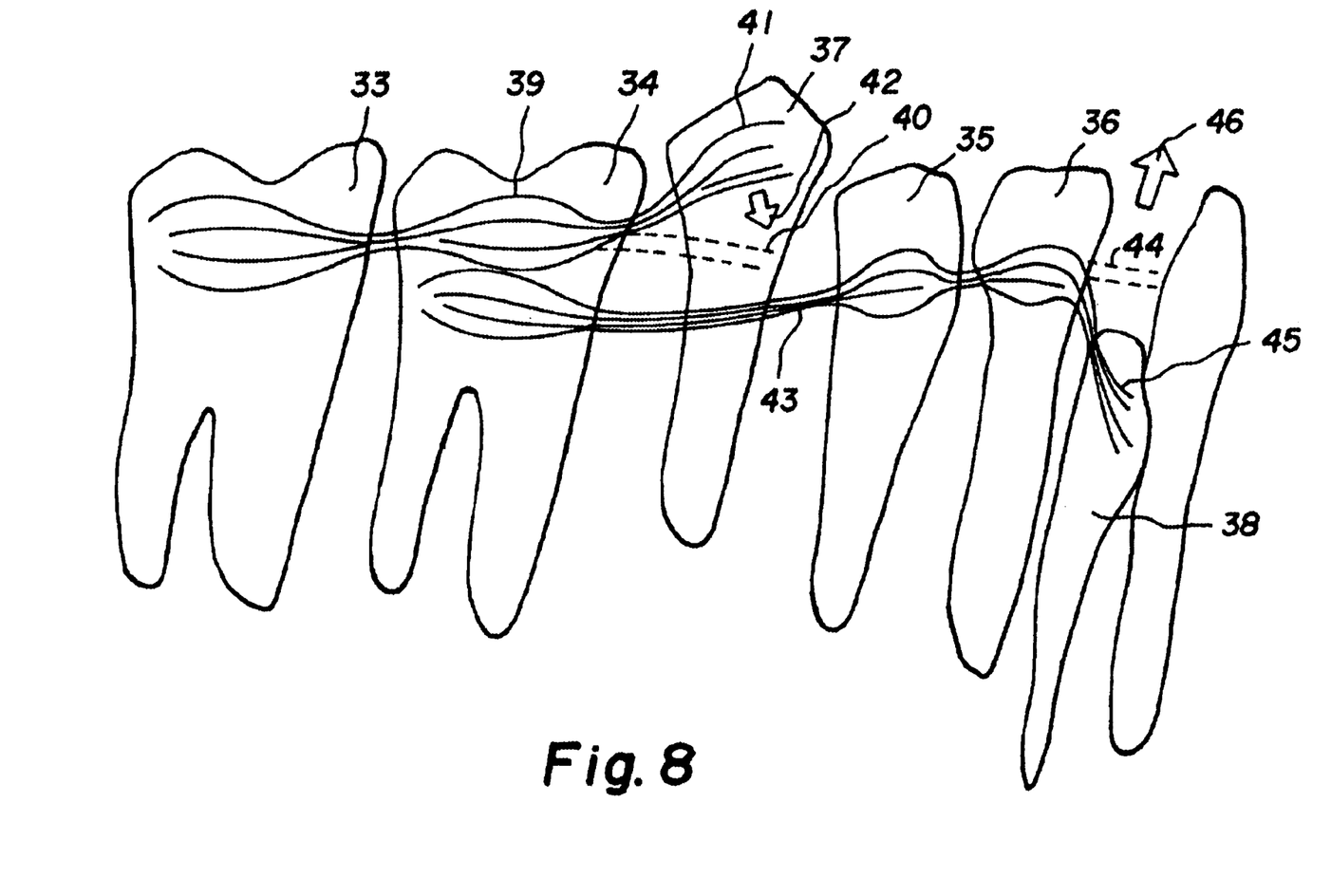
FIG. 8 illustrates an active orthodontic appliance according to an eighth embodiment of the invention.

FIG. 8 illustrates an active orthodontic appliance according to an eighth embodiment of the invention. The Figure shows teeth 33, 34, 35 and 36 that act as anchorage teeth as well as teeth 37 and 38 of which the tooth 37 is to be intruded and the tooth 38 is to be extruded. In a first step, a first part 39 of the appliance is attached to the supporting teeth 33 and 34 and the active part of said first part 39 (showed in dash lines 40) is polymerized. Said active part is then forced to the form shown in 41 whereby an intrusion force in the direction of the arrow 42 is applied to the tooth 37. In a second step, a second part 43 of the appliance is attached to the supporting teeth 34, 35 and 36 and the active part of said second part 43 (again showed in dash lines 44) is polymerized. Said active part is then forced to the form shown in 45 whereby an extrusion force in the direction of the arrow 46 is applied to the tooth 38.

Figure 9:
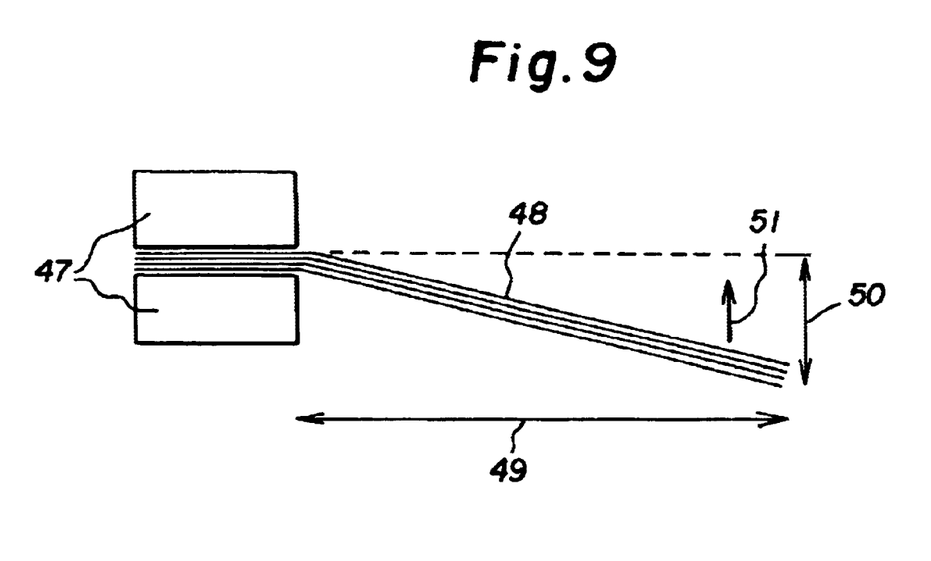
FIG. 9 illustrates the device used for testing the materials used in the invention.

FIG. 9 schematically illustrates the device used for testing the materials used in the invention and will be discussed in detail below.

Figure 10:
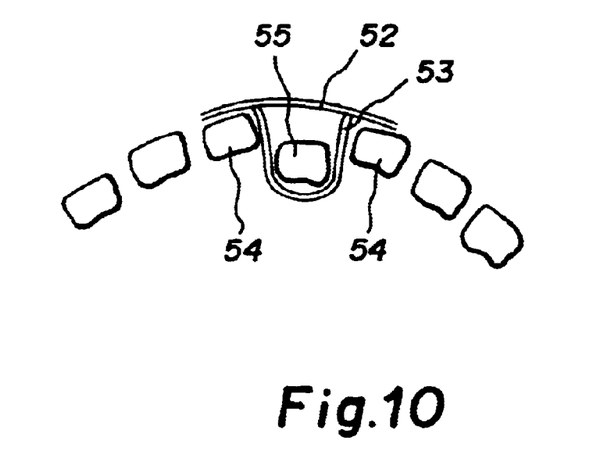
FIG. 10 illustrates an active orthodontic appliance according to a tenth embodiment of the invention.

FIG. 10 illustrates an active orthodontic appliance according to a tenth embodiment of the invention. In this embodiment, the appliance consists of two parts, 52 and 53. The first part 52 is attached to the supporting teeth 54 and the second part 53 forms a loop that is passed over the tooth 55 and does not necessarily need to be attached to it by dental adhesive or the like.

It is obvious to a person skilled in the art that the appliances presented in the Figures may be prepared either in the mouth or on a model. The different parts of the appliances may also be attached to the tooth or teeth at any appropriate moment. According to a preferred embodiment when the appliance is prepared in the mouth of the patient, the first portion of the appliance is attached to the supporting teeth after curing and before forming the second portion of the appliance.

Experimental Part

In this part, the mechanical properties of some commercial prepregs were measured.

EXAMPLE 1

A fiber-reinforced prepreg OrthoStick® prepared by StickTech Oy, Turku, Finland having a diameter of 0.5 mm and fiber volume of 60 vol-% was polymerized with a light curing hand device (Elipar from Espe, Seefeld, Germany).

The flexural properties of OrthoStick® were measured with three point bending test according to ISO 10477 (span 10 mm, loading speed 1.0 mm/min). Flexural strength of 1150 MPa (SD=250) and flexural modulus 26 GPa (Standard deviation SD=1.3 GPa) was measured.

EXAMPLE 2

A bar of OrthoStick® polymerized as in Example 1 having a diameter of 0.5 mm was fixed from the first end to a cantilever jig. The second end of the bar was deflected to a distance of 4 mm from the first end, the span being 10 mm.

The deflection was kept constant over the measurement time. The experimental arrangement is shown in FIG. 9, wherein 47 illustrates the cantilever jig, 48 the bar to be tested, 49 is the span (10 mm), 50 is the deflection (4 mm) and 51 is the force F.

During the first 15 min, the force (F) was creeping from 1.7 N to 0.9 N, after that the load was stabilized to 0.9 N for 60 minutes.

Commonly used nickel-titanium orthodontic wire having a rectangular cross section (0.4×0.4) produced in the same test condition a force (F) of 0.6 N.

The fiber composite materials tested are thus suitable for use in the inventive appliance.

What is claimed is:

1. An active orthodontic appliance, wherein it consists essentially of an arch wire in at least one part, directly contactable with teeth and consisting essentially of a fiber-reinforced composite comprising at least two fibers and a matrix, said fibers being at a first distance from each other on the tooth enamel surface and at a second distance from each other between the teeth, and that said second distance is essentially smaller than said first distance, said arch wire comprising a portion directly contactable with a tooth or teeth to be moved by the appliance.

2. The orthodontic appliance according to claim 1, wherein said arch wire is in one part.

3. The orthodontic appliance according to claim 1, wherein said arch wire is in at least two parts wherein a first part consists of the arch wire directly contactable with a supporting tooth or teeth and an at least second part consists of said portion in the form of a loop directly contactable with the tooth or teeth to be moved by the appliance.

4. The orthodontic appliance according to claim 1, wherein said at least one fiber is selected from the group consisting of glass fibers, silica fibers, quartz fibers, carbon fibers, ceramic fibers, polyolefin fibers, fibers prepared from copolymers of olefins, aramide fibers, polyester fibers, polyamide fibers, polyacrylic fibers and combinations thereof.

5. The orthodontic appliance according to claim 1, wherein said at least one fiber is selected from staple fibers and continuous fibers.

6. The orthodontic appliance according to claim 1, wherein the matrix in its non-cured form is selected from the group consisting of methyl methacrylate, ethyleneglycol dimethacrylate, bis-hydroxy-methacryloxyphenyl propane, triethyleneglycol dimethacrylate, polymethyl methacrylate, urethan dimethacrylate, epoxies, esters, acrylics, sulfones, carbonates, dendrimers and combinations thereof.

7. The orthodontic appliance according to claim 1, wherein the orientation of the fibers in said composite are continuous unidirectional, bi-directional, tri-directional or any combination thereof.

8. A process for manufacturing an active orthodontic appliance comprising the steps of:
 a) shaping a first portion of a prepreg consisting of a composition comprising at least one fiber and a matrix in its non-cured form, to the shape of the tooth or teeth to be used as support for the appliance,
 b) shaping a second portion of the prepreg to the shape of the tooth or teeth to be obtained by the appliance,
 c) curing said prepreg to obtain a composite, and
 d) forcing the second portion of the composite obtained to the original shape of the tooth or teeth to be moved by the appliance.

9. The process according to claim 8, wherein it further comprises a second curing step e) after the step a) and before the step b) in which step said first portion of the prepreg is cured to obtain a first portion of a composite.

10. The process according to claim 9, wherein said curing in steps c) and e) is induced by electromagnetic radiation independently selected from the group consisting of visible light, ultra-violet light, blue light and laser irradiation.

11. The process according to claim 9, wherein said matrix is autopolymerizable and that the curing in steps c) and/or e) is induced by applying an activator on the prepreg.

12. An active orthodontic method of treatment comprising the steps of
 a) shaping a first portion of a prepreg consisting of a composition comprising at least one fiber and a matrix in its non-cured form, to the shape of the tooth or teeth to be used as support,
 b) shaping a second portion of the prepreg to the shape at the end of the orthodontic treatment,
 c) curing said prepreg to obtain a composite,
 d) forcing said second portion of the composite to the shape at the beginning of the orthodontic treatment to obtain an orthodontic appliance, and
 e) contacting said appliance to said teeth for the duration of said treatment.

13. Method of treatment according to claim 12, wherein said method further comprises a step f) between steps a) and b) consisting of curing said first portion of the prepreg to obtain a first portion of a composite.

14. Method of treatment according to claim 13, wherein said method further comprises a step g) between steps f) and b) consisting of attaching said first part of the composite to the tooth or teeth to be used as support.

15. Method of treatment according to claim 14, wherein the composite is in steps e) and/or g) attached to each individual tooth by means of a dental adhesive.

16. Method of treatment according to claim 13, wherein said curing in steps c) and f) is induced by electromagnetic radiation independently selected from the group consisting of visible light, ultra-violet light, blue light and laser irradiation.

17. Method of treatment according to claim 13, wherein said matrix is autopolymerizable and that the curing in steps c and/or f is induced by applying an activator on the prepreg.

18. Method of treatment according to claim 12, wherein said prepreg is in one part.

19. Method of treatment according to claim 12, wherein said prepreg is in at least two parts.

20. Method of treatment according to claim 12, wherein said composite is directly in contact with said tooth or teeth.

21. Method of treatment according to claim 14, wherein said composite is directly attached to said tooth or teeth.

22. Method of treatment according to claim 12, wherein said fiber is selected from the group consisting of glass fibers, silica fibers, quartz fibers, carbon fibers, ceramic fibers, polyethene fibers, polypropene fibers, aramide fibers, polyester fibers, polyamide fibers, polyacrylic fibers and combinations thereof.

23. Method of treatment according to claim 12, wherein the matrix in its non-cured form is selected from the group consisting of methyl methacrylate, ethyleneglycoldimethacrylate, bis-hydroxy-methacryloxyphenyl propane, triethyleneglycol dimethacrylate, polymethyl methacrylate, urethan dimethacrylate dendrimers and combinations thereof.

24. Method of treatment according to claim 12, wherein the orientation of the fibers in said composite is continuous unidirectional, bi-directional, tri-directional or any combination thereof.

\* \* \* \* \*